United States Patent
Russmann et al.

(10) Patent No.: US 9,320,436 B2
(45) Date of Patent: Apr. 26, 2016

(54) METHOD AND DEVICE FOR DETECTING DEPOSITS IN THE EYE

(75) Inventors: Christoph Russmann, Jena (DE); Martin Hacker, Jena (DE); Manfred Dick, Jena (DE); Ingrid Hilger, Jena (DE); Werner A. Kaiser, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 163 days.

(21) Appl. No.: 13/499,624

(22) PCT Filed: Sep. 29, 2010

(86) PCT No.: PCT/EP2010/005922
§ 371 (c)(1),
(2), (4) Date: May 31, 2012

(87) PCT Pub. No.: WO2011/038892
PCT Pub. Date: Apr. 7, 2011

(65) Prior Publication Data
US 2012/0229766 A1    Sep. 13, 2012

(30) Foreign Application Priority Data
Sep. 30, 2009    (DE) .......................... 10 2009 043 750

(51) Int. Cl.
*A61B 3/13*    (2006.01)
*A61B 5/00*    (2006.01)

(52) U.S. Cl.
CPC ............... *A61B 5/0059* (2013.01); *A61B 3/13* (2013.01); *A61B 5/0066* (2013.01); *A61B 5/4088* (2013.01); *A61B 5/4064* (2013.01)

(58) Field of Classification Search
CPC ............ A61B 3/102; A61B 3/12; A61B 3/14; A61B 5/0059; A61B 5/0066; A61B 5/4088; A61B 3/13; A61B 3/135
USPC .................... 351/206, 246, 205; 600/558
See application file for complete search history.

(56) References Cited

U.S. PATENT DOCUMENTS 6,988,995 B2    1/2006    Zhou et al.
7,409,040 B2    8/2008    Cyrulnik
(Continued)

FOREIGN PATENT DOCUMENTS

DE          103 60 570 A1    7/2005
DE    10 2006 030 382 A1    1/2008
(Continued)

OTHER PUBLICATIONS

Volker Luibl et al. "Drusen deposits associated with aging and age-related macular degeneration contain nonfibrillar amyloid oligomers," Feb. 1, 2006, Journal of Clinical Investigation, vol. 116(2), pp. 378-385.*
(Continued)

*Primary Examiner* — Thomas K Pham
*Assistant Examiner* — Marin Pichler
(74) *Attorney, Agent, or Firm* — Patterson Thuente Pedersen, P.A.

(57) ABSTRACT

A method and devices for detecting deposits, in particular amyloid plaques, in the eye, in particular in the human eye. The subject is an optical method for detecting deposits, in particular β-amyloid, in the retina, which is locally resolved and wherein the local resolution is better than the layer thickness of individual layers of the retina. The invention includes a device for optically detecting β-amyloid in the retina, which generates a locally resolved image of the retina and wherein the local resolution is better than the layer thickness of individual layers of the retina.

13 Claims, 2 Drawing Sheets

(56) References Cited

U.S. PATENT DOCUMENTS

| | | | |
|---|---|---|---|
| 2004/0116436 A1* | 6/2004 | Tatton et al. | 514/249 |
| 2004/0152068 A1 | 8/2004 | Goldstein et al. | |
| 2006/0148905 A1* | 7/2006 | Kim | 514/679 |
| 2007/0013918 A1 | 1/2007 | Hauger et al. | |
| 2009/0304591 A1 | 12/2009 | Russmann et al. | |
| 2011/0200531 A1* | 8/2011 | Tan | 424/9.2 |

FOREIGN PATENT DOCUMENTS

| | | |
|---|---|---|
| DE | 10 2007 061 9 | 6/2009 |
| WO | WO 2008/000403 A2 | 1/2008 |
| WO | WO 2009/083159 A1 | 7/2009 |

OTHER PUBLICATIONS

Goldstein, Lee E., et al., "Cytosolic β-amyloid deposition and supranuclear cataracts in lenses from people with Alzheimer's disease," *The Lancet*, vol. 361, Apr. 12, 2003, pp. 1258-1265.

Dentchev, Tzvete, et al., "Amyloid-β is found in drusen from some age-related macular degeneration retinas, but not in drusen from normal retinas," *Molecular Vision*, vol. 9, 2003, pp. 184-190.

Bayer, A.U., et al., "High Occurrence Rate of Glaucoma among Patients with Alzheimer's Disease," *European Neurology*, vol. 47, 2002, pp. 165-168.

Anderson, Don H., et al., "Characterization of β amyloid assemblies in drusen: the deposits associated with aging and age-related macular degeneration," *Experimental Eye Research*, vol. 28, 2004, pp. 243-256.

Wang, Jiying, et al., "Altered Function of Factor 1 Caused by Amyloid β: Implication for Pathogenesis of Age-Related Macular Degeneration from Drusen," *The Journal of Immunology*, vol. 181, 2008, pp. 712-720.

Vickers, JC, "The cellular mechanism underlying neuronal degeneration in Glaucoma: Parallels with Alzheimer's disease," *Australian and New Zealand Journal of Ophthalmology*, vol. 25, 1997, pp. 105-109.

Parisi, Vincenzo, "Correlation between morphological and functional retinal impairment in patients affected by ocular hypertension, glaucoma, demyelinating optic neuritis and Alzheimer's disease," *Seminars in Ophthalmology*, vol. 18, No. 2, 2003, pp. 50-57.

Gupta, Neeru, et al., "Retinal tau pathology in human glaucomas," *Can J. Opthalmol*, vol. 43, No. 1, 2008 (pp. 53-.

\* cited by examiner

METHOD AND DEVICE FOR DETECTING DEPOSITS IN THE EYE

PRIORITY CLAIM

The present application is a National Phase entry of PCT Application No. PCT/EP2010/05922, filed Sep. 29, 2010, which claims priority from German Application No 102009043750.9, filed Sep. 30, 2009, the disclosures of which are hereby incorporated by reference herein in their entirety.

FIELD OF THE INVENTION

The invention relates to a method and devices for detecting deposits, particularly amyloid plaques, in the eye, particularly in the human eye.

The detection of amyloid plaques is of particular interest in conjunction with the diagnosis of the so-called Alzheimer's disease (Morbus Alzheimer).

Morbus Alzheimer is a disease which typically occurs at an older age and causes increasing loss of cognitive and non-cognitive abilities in the afflicted patient. β-amyloid plaques as well as pathologically altered nerve cell processes with intracellularly positioned fibrillar deposits of the τ-PHF protein form in the brain of patients with Morbus Alzheimer.

During the course of the disease, the brain mass decreases due to necrotizing neurons, which is referred to as brain atrophy. The presence of β-amyloid plaques in the cerebral cortex is an acknowledged early pathological sign of Morbus Alzheimer. The β-amyloid pathology starts in the cerebral cortex while the τ-PHF pathology initially occurs in the hippocampal formation.

However, the detection of β-amyloid plaques in the brain of patients is very difficult.

For this purpose, U.S. Pat. No. 7,409,040 suggests a method and a device for detecting pathological macromolecules in the brain on the basis of X-ray analysis or microwave/high-frequency analysis which, however, is very elaborate and, according to the applicant's knowledge, has not yet been realized.

It is known that β-amyloid deposits are also found in the crystalline lens (Goldstein L E, Muffat J A, Cherny R A, Moir R D, Ericsson M H, Huang X, (2003) Cytosolic beta-amyloid deposition and supranuclear cataracts in lenses from people with Alzheimer's disease. Lancet.; 36:1258-65), der Retina (Parisi V. (2003) Correlation between morphological and functional retinal impairment in patients affected by ocular hypertension, glaucoma, demyelinating optic neuritis and Alzheimer's disease. Semin Ophthalmol.; 18(2):50-7), and in blood vessels.

Furthermore, there is evidence for deposits of τ-PHF in the retina (Gupta N, Fong J, Ang L C, Yücel Y H. Retinal tau pathology in human glaucomas. Can J Ophthalmol. 2008 February; 43(1):53-60)

It is also known that Morbus Alzheimer patients increasingly suffer from eye diseases such as AMD and glaucoma (cf. Bayer A U, Ferrari F, Erb C. High occurrence rate of glaucoma among patients with Alzheimer's disease. Eur Neurol. 2002; 47(3):165-8) or Vickers J C. (1997) The cellular mechanism underlying neuronal degeneration in glaucoma: parallels with Alzheimer's disease. Aust N Z J Ophthalmol.:105-9. Review).

Therefore, there are a number of suggestions to facilitate an Alzheimer's diagnosis through measurements on the eye.

U.S. Pat. No. 7,297,326 suggests the verification of the presence of β-amyloid deposits in the lens using special fluorescence markers which are brought in contact with the eye tissue and subsequently wander into the crystalline lens. A binding of the markers to β-amyloid is then deduced from an analysis of the fluorescence. However, this examination can no longer be performed on patients whose natural crystalline lens had to be removed due to a cataract.

In U.S. Pat. No. 6,988,995, it is attempted to detect the loss of ganglion cells in the retina using a polarimeter and to subsequently diagnose Alzheimer's.

The entire contents of applicant's DE 10 2007 061987 are hereby incorporated herein by reference, which suggest the use of a laser scanning ophthalmoscope (LSO) for verifying β-amyloid deposits in the crystalline lens.

The entire contents of the applicant's DE 10 2006 030382 are hereby incorporated herein by reference, which describe different markers and optical detection methods for verifying, among others, β-amyloid in the eye.

Furthermore, it is known that β-amyloid can also be found in the drusen of patients with age-related macular degeneration (AMD) (Dentchev T, Milam A H, Lee V M, Trojanowski J Q, Dunaief: "Amyloid-beta is found in drusen from some age-related macular degeneration retinas, but not in drusen from normal retinas" Mol Vis. 2003 May 14; 9:184-90 and Anderson D H, Talaga K C, Rivest A J, Barron E, Hageman G S, Johnson L V: "Characterization of beta amyloid assemblies in drusen: the deposits associated with aging and age-related macular degeneration.", Exp Eye Res. 2004 February; 78(2): 243-56) and that β-amyloid is, among others, involved in the further progress of AMD which leads to "geographic atrophy" (final stage of dry AMD) or choroidal neovascularization (CNV, wet AMD) (Wang J, Ohno-Matsui K, Yoshida T, Kojima A, Shimada N, Nakahama K, Safranova O, Iwata N, Saido T C, Mochizuki M, Morita I.: "Altered function of factor I caused by amyloid beta: implication for pathogenesis of age-related macular degeneration from Drusen.", J Immunol. 2008 Jul. 1; 181(1):712-20.).

Therefore, the previous methods which use the verification of β-amyloid as evidence for the presence of Morbus Alzheimer can be massively distorted and even lead to misdiagnoses due to the presence of β-amyloid deposits caused by AMD.

SUMMARY OF THE INVENTION

Therefore, the invention addresses the problem of overcoming the disadvantages of the prior art and seeks to provide more reliable methods for detecting deposits in the eye.

According to the invention, this problem is solved with an optical method for detecting deposits, particularly β-amyloid in the retina, which is locally resolved and wherein the local resolution is better than the layer thickness of individual layers of the retina, particularly, in one example, the local resolution is better than 20 μm, in another example, better than 10 μm, and in a further example, better than 5 μm.

An advantageous embodiment of the method according to the invention is achieved when the β-amyloid is marked with appropriate molecular markers and layer-selectively detected. The following are particularly suitable as markers:

Thioflavin S and its derivatives (e.g. Pittsburgh Compound B) (IUPAC 4-(3,6-dimethyl-1,3-benzothiazol-3-ium-2-yl)-N,N-dimethylaniline chloride);

Thioflavin T (IUPAC: 4-(3,6-dimethyl-1,3-benzothiazol-3-ium-2-yl)-N,N-dimethylaniline chloride) and its derivatives;

Congo red and its derivatives (IUPAC: 3,3'-(4,4' biphenyldiylbisazo)bis-(4-amino-1-naphthalene sulfonic acid)-disodium salt);

Methylene blue (Rember) (3,7-bis(dimethylamino)-phenothiazinium chloride) and its derivatives;

β-amyloid-specific antibodies, antibody fragments, peptides, aptamers, RNA molecules with intrinsic or extrinsic properties, which are suitable for optical depiction (e.g. through adding a colorant such as indocyanine green or fluorescein or a substance for increasing the absorbent or scattering properties such as "gold nanocages", or "microspheres" with melanin or gold).

It is particularly advantageous if the local resolution is suitable for resolving the morphological structure of the β-amyloid deposits.

The following are particularly suitable for executing the method according to the invention: High-resolution OCT (optical coherence tomography) devices, high-resolution fundus cameras, high-resolution laser scanning ophthalmoscopes, a polarimeter, or a combination of the previously mentioned devices, and the like.

Furthermore, the problem addressed by the invention is solved through a device for the optical detection of β-amyloid in the retina which produces a locally resolved image of the retina and wherein the local resolution is better than the layer thickness of individual layers of the retina, particularly, in one example, the local resolution is better than 20 µm, in another example, better than 10 µm, and in a further example, better than 5 µm.

Such a device can, e.g. comprise a high-resolution OCT (optical coherence tomography) device, a high-resolution fundus camera, a high-resolution laser scanning ophthalmoscope, a polarimeter, or a combination of the previously mentioned devices, and the like.

The previously described method can, according to the invention, also be used for detecting deposits of τ-PHF in the retina.

The layer-selective analysis of Alzheimer-specific plaques is advantageous, e.g. within the described methods through combining a high-resolution fundus imaging on the basis of the marker-specific fluorescence and a high-resolution OCT cross-sectional imaging particularly in the areas of pronounced marker-specific fluorescence because it allows for a morphological evaluation of the areas detected on a molecular basis. As a result, an easier, marker-free, morphological therapy control, according to the invention, is possible, particularly with exact registration of the affected areas detected on a molecular basis for a three-dimensional morphology, particularly with the help of combination devices.

Such combination devices are, for example, a wide field fundus camera with color image fluorescence excitation and/or autofluorescence excitation and spectrally selective excitation and detection modalities in registered conjunction with methods of the optical coherence tomography (OCT) which allows for a three-dimensional, high-resolution, morphological but "molecularly" assigned imaging.

Further combinations, according to the invention, are confocal laser scanning methods which are already capable of detecting three-dimensionally, molecularly assigned fluorescences and which have a registered, i.e. geometrically matching, OCT system for pure monitoring and therapy control assigned to them.

According to the invention, the combination of marker-bound OCT methods with polarization methods, confocal scanning methods of fundus imaging methods is also provided.

With all these possible combinations, it is important that the more invasive, molecular-specific imaging which requires the administering of molecular probes is combined in registered fashion for a follow-up or therapy control with less invasive but high-resolution imaging methods in order to ensure an unambiguous assignment of molecular findings to morphological findings.

According to the invention, a marker-based fluorescence analysis on a molecular level (fundus camera fluorescence analysis) is therefore performed with a combination device which is subsequently followed by a spatially registered morphological tissue analysis (e.g. OCT) for the follow-up.

BRIEF DESCRIPTION OF THE DRAWINGS

In the following, the invention is further described by means of drawings.

DETAILED DESCRIPTION

Figure 1:
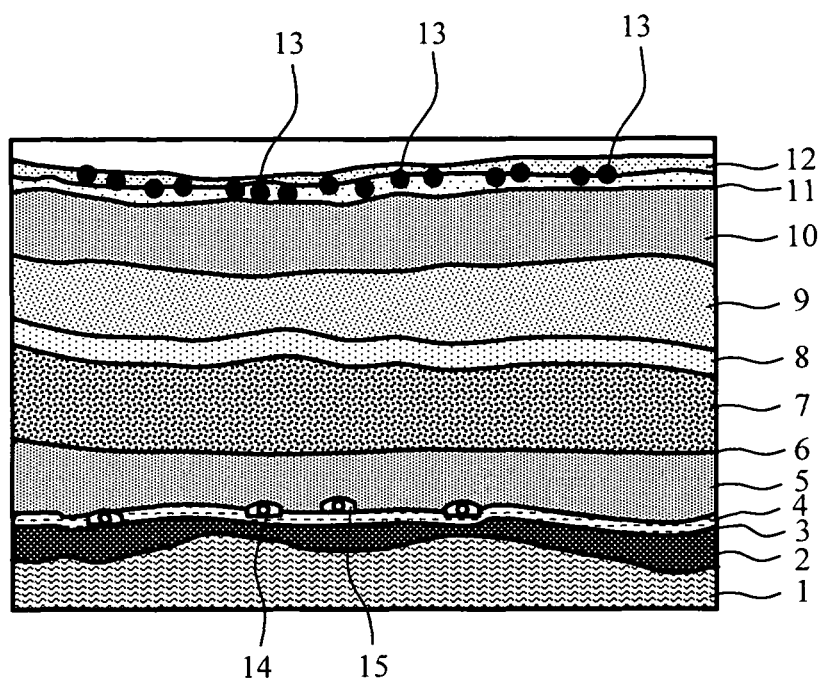
FIG. 1 depicts a cross-section of the retina.

FIG. 1 shows a cross-section of the retina of the eye to illustrate the layered structure. In this depiction, the light focused through cornea and lens impinges on the retina from below. The sclera 1 is followed in sequence by the following layers: Choroid 2, Bruch's membrane (lamina vitrea) 3, retinal pigment epithelium 4, rods and cones 5, outer limiting membrane 6, external granular layer 7, outer plexiform layer 8, internal granular layer 9, inner plexiform layer 10, ganglion cell layer 11, and retinal nerve fiber layer (RNFL) 12.

The entire thickness of the retina is approximately 200-300 µm.

β-amyloid deposits 13 are enclosed in the retinal nerve fiber layer 12 and the ganglion cell layer 11.

At Bruch's membrane 3, drusen 14 are present which also contain β-amyloid deposits 15.

Thereby, the enclosed β-amyloid deposits 13 in the retinal nerve fiber layer 12 and the ganglion cell layer 11 are characteristic for Alzheimer's while the presence of β-amyloid in the drusen 14 suggests AMD.

Figure 2:
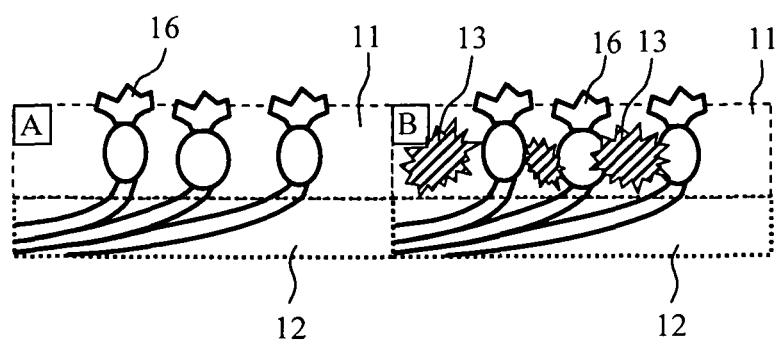
FIG. 2 depicts a schematic depiction of the ganglion cell layer.

FIG. 2 shows a schematic depiction of the ganglion cell layer 11; in (A), the ganglia 16 have a roundish to oval shape and do not lie very close together. (B) shows the deposits of β-amyloid 13 which are located between the ganglia 16 and already morphologically distinguishable from said ganglia.

Figure 3:
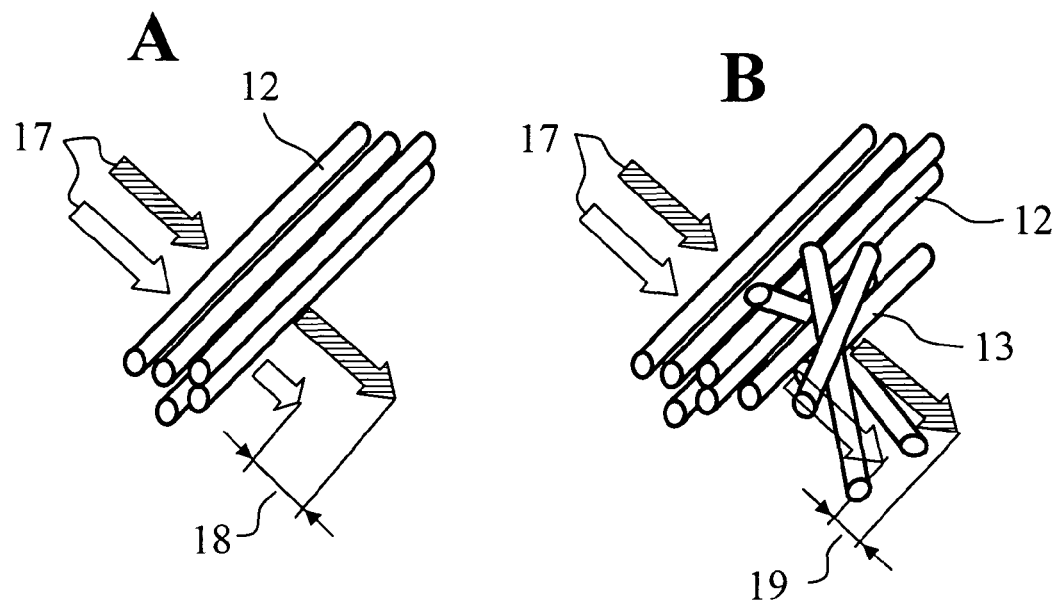
FIG. 3 depicts a schematic depiction of the retinal nerve fiber layer.

FIG. 3 schematically depicts the fundamentals for a polarimetric determination of the presence of β-amyloid. In (A), light 17, which is vertically polarized to each another, is delayed in characteristic fashion by the relatively regular retinal nerve fiber layer 12, causing a delay 18 determined by the thickness of the RNFL 12. In (B), an additional inhomogeneous delay component is introduced by the β-amyloid deposits 13, and therefore the resulting delay 19 differs from the "undisturbed" delay 18. As a result, the presence of β-amyloid deposits 13 can be verified with a polarimeter as shown in U.S. Pat. No. 6,988,995, the entire content of which is hereby incorporated herein by reference, through a comparison with appropriate standard values or databases.

Figure 4:
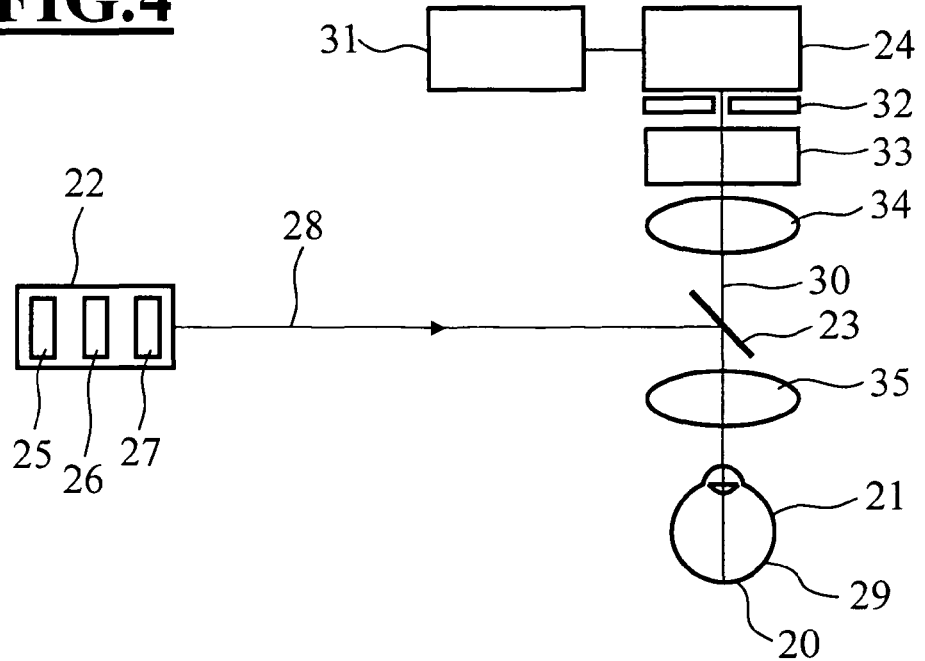
FIG. 4 depicts a schematic depiction of a laser scanning ophthalmoscope.

FIG. 4 shows an embodiment of a device for verifying β-amyloid molecules 20 in an eye 21 in the form of a laser scanning ophthalmoscope. The device comprises a laser scanner 22, a mirror with dichroic coating 23, and a photomultiplier 24. The laser scanner 23 has a laser 25, a scan module 26 which is made of two galvano scanners and a variable expander, and an additional modulator 27.

The photomultiplier 24 is arranged opposite of the eye 21. The mirror with dichroic coating 23 is arranged between the eye 21 and the photomultiplier 24 and aligned at a 45° angle to a connecting line between the eye 21 and the photomultiplier 24. The laser scanner 22 is arranged at a distance from the mirror with dichroic coating 23 in such a way that a connecting line between the mirror with dichroic coating 23 and the laser scanner 22 forms an angle of 135° with the mirror with dichroic coating 23.

The laser 22 produces a laser beam 28 which is aligned through both galvano scanners and the variable expander and the wavelength of which is adjusted by the power modulator 27 to 360-370 nm or a wavelength in the visible or infrared spectral range suitable for the excitation of appropriate molecular markers. The laser beam 28 impinges on the mirror with dichroic coating 23 and is partially directed toward the retina 29 of the eye 21. The laser beam 28 causes autofluorescence of the β-amyloid molecules 20 in the retina 29 or fluorescence of molecular markers specifically bound to β-amyloid. As a result, they emit light with a wavelength of more than 420 nm. This light forms a light beam 30. The light beam 30 partially passes through the mirror with dichroic coating 23 and impinges on the photomultiplier 24. The photomultiplier 24 detects the fluorescent light emitted from the β-amyloid molecules 20 or the molecular marker.

As a result, it can easily be determined whether β-amyloid molecules 20 are present in the retina 29 of an eye 20.

As a rule, the absorption spectra of the target molecules are relatively broad, and therefore, depending on the embodiment, a variation of the laser wavelength by 20 nm is possible.

In addition, the device comprises a lock-in amplifier 31, a detector aperture 32, a filter 33, a transfer lens 34, and a focusing lens 35.

The focusing lens 35 is arranged between the eye 21 and the mirror with dichroic coating 23 in the area of the laser beam 28. The transfer lens 34, the color filter 33, and the detector aperture 32 are arranged between the photomultiplier 24 and the mirror with dichroic coating 23 in the area of the light beam 30.

The lock-in amplifier 31 is connected to the photomultiplier 24.

The laser beam 28 is focused through the focusing lens 35, and therefore has a very small profile in the area of the retina 29. The light beam 30 is focused through the transfer lens 34. Portions of the light beam 30, which are not emitted by a β-amyloid molecule, are filtered out by the color filter 33. The detector aperture 32 suppresses unwanted stray light portions. The lock-in amplifier 31 processes the signal from the detector in such a way that the signal-to-noise ratio is increased during detection.

By providing the focusing optics 35, it is possible to scan the retina 29 with a high resolution. Thereby, the resolution can be selected at such a level that autofluorescence and fluorescence images of the retina 29 can be produced. By providing the color filter 33 and the detector aperture 32, unwanted portions from the light beam 30 are filtered or blocked out. Since the light beam 30 is focused through the transfer lens 34, a higher energy density is achieved in the focus of the light beam 30. This simplifies a detection of the light beam 30.

The requirements for the verification of β-amyloid in the retina are outlined in the following table:

| Parameters | Value |
| --- | --- |
| Retina | |
| Thickness of the Retina | 200-300 μm |
| Thickness ganglion cell layer | 20-30 μm |
| Thickness retinal pigment epithelium | 20-30 μm |
| Thickness Bruch's membrane | 2 μm |
| β-Amyloid plaques in the ganglion cell layer: | |
| Size | 5 bis >50 μm (partial clustering) |
| Properties | Fibrillar structure "green" double refraction |
| Absorption maxima Emission maxima | 360-370 nm >420 nm |
| β-Amyloid in the drusen: | |
| Drusen | Classification: Dry AMD: 63-124 μm Intermediate AMD: >125 μm |

A number of methods are possible for detecting β-amyloid in the retina:

1. Layer-Selective Verification Through Marker-Based Methods.

With the help of molecular markers, which are specific against β-amyloid and/or τ-PHF, β-amyloid plaques and/or τ-PHF plaques can be verified layer-selectively in conjunction with a suitable imaging device.

Molecular Marker

Among others, the following β-amyloid-specific markers are applicable:

- Thioflavin S and its derivatives (e.g. Pittsburgh Compound B) (IUPAC 4-(3,6-dimethyl-1,3-benzothiazol-3-ium-2-yl)-N,N-dimethylaniline chloride);
- Thioflavin T (IUPAC: 4-(3,6-dimethyl-1,3-benzothiazol-3-ium-2-yl)-N,N-dimethylaniline chloride) and its derivatives;
- Congo red and its derivatives (IUPAC: 3,3'-(4,4' biphenyldiylbisazo)bis-(4-amino-1-naphthalene sulfonic acid)-disodium salt);

as well as

- Methylene blue (Rember) (3,7-bis(dimethylamino)-phenothiazinium chloride) and its derivatives;
- β-amyloid-specific antibodies, antibody fragments, peptides, aptamers, RNA molecules with intrinsic or extrinsic properties, which are suitable for optical depiction (e.g. through adding a colorant).

Thiazo-hydrazide and its derivatives as well as τ-PHF-specific antibodies, antibody fragments, peptides, aptamers, RNA molecules with intrinsic or extrinsic properties, which are suitable for optical depiction, are provided as τ-PHF-specific markers.

Imaging Device

The following devices (or combinations thereof) can be used as imaging device:

- Optical coherence tomography;
- High-resolution laser scanning ophthalmoscope (LSO) (see FIG. 4), scanning ophthalmoscope with superluminescent diode (SLD);
- Fundus cameras with spectral-dependent penetration depth, e.g. through the use of light in the blue spectral range, which only excites the anterior segments of the retina and also causes a type of layer selectivity.

The verification can be made possible directly through visualization of the plaques in the respective layer but also automatically with a software-based image analysis in conjunction with a segmentation and a feature extraction as well as comparison with a normative database.

Plaques in the ganglion cell layer indicate Morbus Alzheimer while plaques in the sub-RPE (retinal pigment layer) indicate AMD.

2. Layer-Selective Verification Through High-Resolution Imaging.

β-amyloid plaques in the ganglion cell layer are verified with the help of a high-resolution imaging method. Thereby, the imaging device must be capable of meeting the marginal conditions in the table above.

The bodies of the ganglion cells have a roundish to oval shape and do not lie very close together (cf. FIG. 2). The β-amyloid plaques exhibit a different morphology and also interrupt the position of the ganglion cell layer.

Imaging Device

Verification is achieved through the recording of a high-resolution image of the posterior eye segments, e.g. with one of the following imaging devices:

High-resolution optical coherence tomography (resolution <20 μm);
High-resolution laser scanning ophthalmoscope (LSO) (see FIG. 4), scanning ophthalmoscope with superluminescent diode (SLD);
High-resolution fundus cameras with spectral-dependent penetration depth and/or structured illumination;
A combination of the above-mentioned devices (e.g. OCT and fundus camera)

In order to improve the resolution, all devices can be combined with adaptive optics.

The detection can be executed through simple visualization of the ganglion cell layer and determination of morphological differences. Furthermore, detection is possible with a software-based image analysis in conjunction with a segmentation and a feature extraction as well as comparison with a normative database.

3. Layer-selective Verification Through Polarization-Sensitive Measurement.

β-amyloid plaques are verified using the polarimetric method, e.g. with a laser scanning polarimeter as known from U.S. Pat. No. 6,988,995.

The method is executed as follows: The relatively regular, birefringent retinal nerve fiber layer (RNFL) delays the phases of light which is vertically polarized to each another (cf. FIG. 3). The randomly oriented and also birefringent β-amyloid plaques—which are positioned in close proximity to the RNFL—alter the phases differently from the regular RNFL which allows for the detection of β-amyloid plaques through comparison with a normative database.

Analogously, τ-PHF plaques in the retina can also be verified with the method according to the invention.

4. Layer-Selective Verification and Therapy Control Through Multimodal Imaging.

The use of molecular markers is a highly sensitive and specific method for detecting β-amyloid plaques and τ-PHF and is preferably used for making the actual diagnosis. In parallel, the fluorescence images can be combined with images from marker-free methods such as OCT, LSO, or polarization method. The morphological changes or the polarization changes can then be assigned to disease-specific molecular changes, e.g. a morphological change can be identified decisively as β-amyloid plaque.

These morphological changes, e.g. size and shape of the plaques, or changes of the polarization behavior can subsequently be used within the course of the medical therapy as non-invasive indicator for the therapeutic success and, if applicable, for the adjustment of the treatment regime.

This method provides a significant cost reduction and risk minimization for the patient because—aside from the actual diagnostic step—it is non-invasive. In addition, the marker-free therapy monitoring allows for a point of care treatment, e.g. application of the method in nursing homes or at resident physicians.

This is conceivable with the use of two separate devices or a combination device, wherein both imaging devices can be coupled into the eye using mirror systems. The images of both devices are combined using appropriate software.

The invention claimed is:

1. A method for detecting β-amyloid deposits in a living retina of an eye, comprising:
   imaging the living retina at a local resolution; and
   selecting the local resolution such that it is better than 10 μm;
   evaluating images from the imaging to discern the location of the deposits within the retina to distinguish Alzheimer's disease from aging related macular degeneration; and
   basing differentiation of Alzheimer's disease from aging related macular degeneration on distinguishing an occurrence of β-amyloid in a retinal nerve fiber layer or a ganglion cell layer of the living retina from the occurrence of β-amyloid in drusen, wherein β-amyloid located in the retinal nerve fiber layer or the ganglion cell layer of the living retina is considered indicative of Alzheimer's disease and wherein β-amyloid located in the drusen is considered indicative of aging related macular degeneration.

2. The method for detecting β-amyloid deposits in the living retina, according to claim 1, further comprising selecting the local resolution to be better than 5 μm.

3. The method for detecting β-amyloid deposits in a living retina, according to claim 1, further comprising marking the β-amyloid with appropriate markers; and detecting the markers in a layer-selective manner.

4. The method for detecting β-amyloid deposits in a living retina, according to claim 3, further comprising selecting at least one marker of the appropriate markers from a group consisting of:
   Thioflavin S (IUPAC 4-(3,6-dimethyl-1,3-benzothiazol-3-ium-2-yl)-N,N-dimethylaniline chloride)) and its derivatives;
   Thioflavin T (IUPAC: 4-(3,6-dimethyl-1,3-benzothiazol-3-ium-2-yl)-N,N-dimethylaniline chloride) and its derivatives;
   Congo red (IUPAC: 3,3'-(4,4' biphenyldiylbisazo)bis-(4-amino-1-naphthalene sulfonic acid)-disodium salt) and its derivatives;
   Methylene blue (3,7-bis(dimethylamino)-phenothiazinium chloride) and its derivatives;
   β-amyloid-specific antibodies, antibody fragments, peptides, aptamers, and RNA molecules with intrinsic or extrinsic properties which are suitable for optical detection.

5. The method for detecting β-amyloid deposits in a living retina, according to claim 1, further comprising selecting the local resolution to be suitable for resolving a morphological structure of the β-amyloid deposits.

6. The method for detecting β-amyloid deposits in a living retina, according to claim 1, further comprising performing the imaging is performed by using one of the following devices: a high-resolution OCT (optical coherence tomography) device, a high-resolution fundus camera, a high-resolution laser scanning ophthalmoscope, a polarimeter, or a combination thereof.

7. The method for detecting β-amyloid deposits in a retina, according to claim 1, further comprising evaluating images from the imaging to analyze a morphology of the deposits in the retina to distinguish Alzheimer's disease from aging related macular degeneration.

8. The method for detecting β-amyloid deposits in a living retina, according to claim 1, further comprising using information acquired to control or treat Alzheimer's disease or aging related macular degeneration.

9. A method for detecting deposits of τ-PHF (Paired Helical Filament) in a living retina comprising:
  imaging the living retina at a local resolution;
  wherein the local resolution is better than 20 μm;
  basing differentiation of Alzheimer's disease from aging related macular degeneration on distinguishing an occurrence of τ-PHF in a retinal nerve fiber layer or in a ganglion cell layer of the retina from the occurrence of τ-PHF in drusen; and
  evaluating images from the imaging to discern the location of the deposits within the retina to distinguish Alzheimer's disease from aging related macular degeneration, wherein τ-PHF located in the retinal nerve fiber layer or the ganglion cell layer of the living retina is considered indicative of Alzheimer's disease and wherein τ-PHF located in the drusen is considered indicative of aging related macular degeneration.

10. The method for detecting deposits of τ-PHF in a living retina, according to claim 9, further comprising evaluating images from the imaging to analyze a morphology of the deposits in the retina to distinguish Alzheimer's disease from aging related macular degeneration.

11. The method for detecting deposits of τ-PHF in a living retina, according to claim 9, further comprising using information acquired to control or treat Alzheimer's disease or aging related macular degeneration.

12. The method for detecting deposits of τ-PHF in a living retina, according to claim 9, wherein the local resolution is better than 10 μm.

13. The method for detecting deposits of τ-PHF in a living retina, according to claim 9, wherein the local resolution is better than 5 μm.

* * * * *